United States Patent [19]
Kilham

[11] Patent Number: 5,509,904
[45] Date of Patent: Apr. 23, 1996

US005509904A

[54] REMOTE DRUG INJECTION DEVICE

[76] Inventor: Benjamin Kilham, P.O. Box 37, Lyme, N.H. 03768

[21] Appl. No.: 294,885

[22] Filed: Aug. 23, 1994

[51] Int. Cl.[6] ............................................. A61M 5/32
[52] U.S. Cl. ........................ 604/192; 604/232; 604/263
[58] Field of Search ..................... 604/192, 232–234, 604/197, 160, 240, 207, 208, 210, 221, 222, 187, 241, 263, 198, 224; 128/919

[56]        References Cited

U.S. PATENT DOCUMENTS

| | | | |
|---|---|---|---|
| D. 196,091 | 8/1963 | Evers et al. | |
| 1,012,700 | 12/1911 | Payne | 604/232 |
| 1,606,034 | 11/1926 | MacGregor | 604/232 |
| 2,859,751 | 11/1958 | Stroop | |
| 2,874,694 | 2/1959 | Blackman | |
| 2,956,563 | 10/1960 | Sarnoff | |
| 2,994,323 | 8/1961 | Dann et al. | 604/232 |
| 3,076,455 | 2/1963 | McConnaughey et al. | 604/232 |
| 3,155,093 | 11/1964 | Enström et al. | |
| 3,209,695 | 10/1965 | Crockford et al. | |
| 3,494,358 | 2/1970 | Fehlis et al. | |
| 3,780,734 | 12/1973 | Wulff | 604/197 |
| 3,840,007 | 10/1974 | Fish | |
| 3,880,162 | 4/1975 | Simmons | |
| 4,594,073 | 6/1986 | Stine | 604/187 |
| 4,643,724 | 2/1987 | Jobe | 604/232 |
| 4,758,233 | 7/1988 | Phillips et al. | 604/232 |
| 5,360,409 | 11/1994 | Boyd, III et al. | 604/198 |
| 5,389,083 | 2/1995 | McCarthy | 604/192 |

OTHER PUBLICATIONS

New England Medical Technologies, Inc. Sales brochure—Safety Stick.

*Primary Examiner*—C. Fred Rosenbaum
*Assistant Examiner*—V. Alexander
*Attorney, Agent, or Firm*—Michael J. Weins

[57]        ABSTRACT

The present invention is for a remote drug injection device which is suitable for use with a standard hypodermic syringe. The device has a tube which has a front rim and rear rim and a tube axis. The tube has a syringe section having a longitudinal syringe engaging passage configured to grippably engage the syringe. The tube has a plunger section having a plunger passage with a cross section configured to accommodate the plunger. The tube has a rear section having a rear passage. The three tube passages are arranged so that their axis forms the tube axis. A syringe insertion passage passing through the syringe section of the tube is provided. The syringe insertion passage has an axis which intersects the tube axis. A bottom syringe passage opening extends form the front rim of the tube and joins the syringe insertion passage. Similarly, a top syringe passage opening is provided from the syringe insertion passage and extends to the plunger section. The plunger section has a plunger section opening which joins the top opening. A shaft is provided which slidably engages the rear passage of the tube.

15 Claims, 7 Drawing Sheets

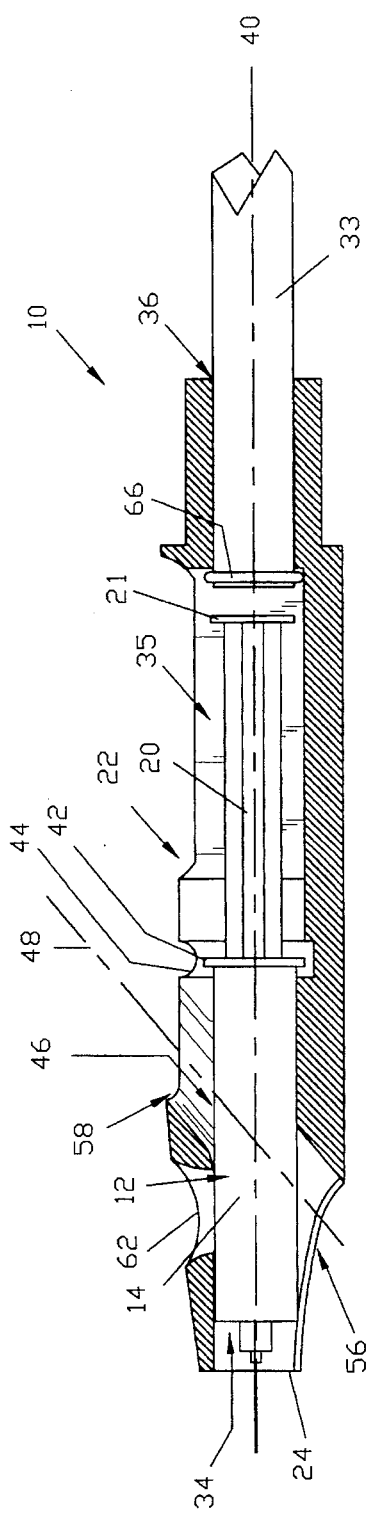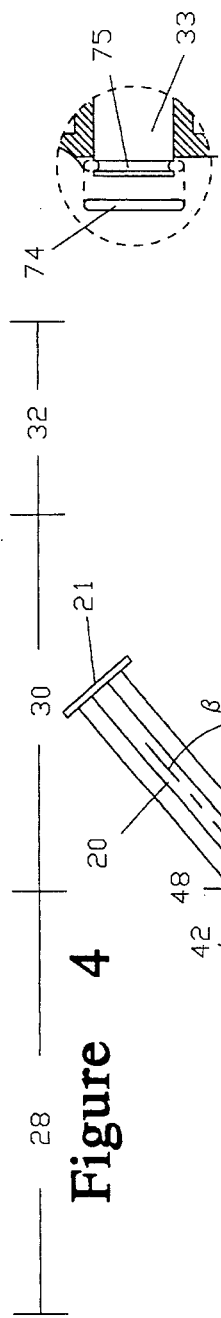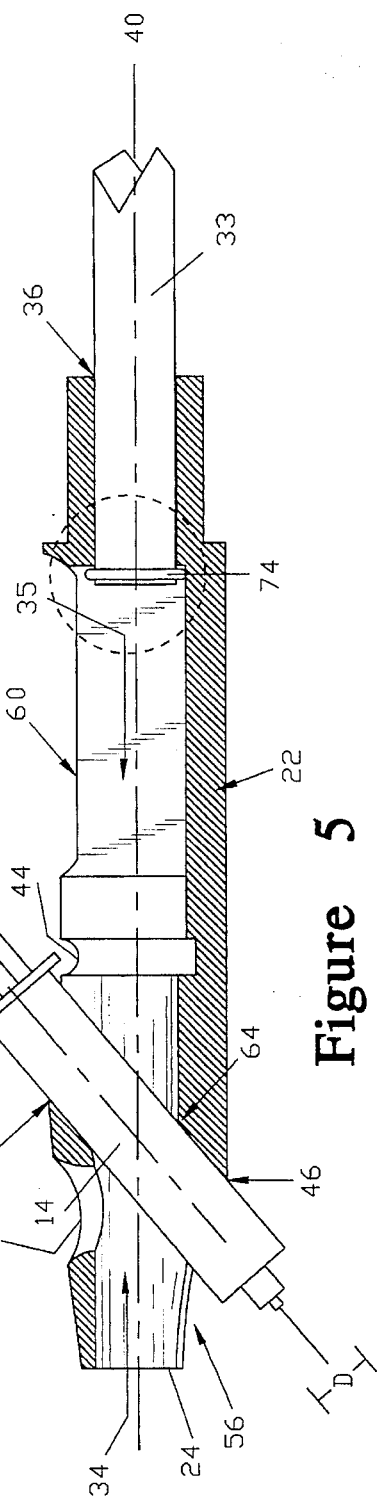

REMOTE DRUG INJECTION DEVICE

FIELD OF THE INVENTION

The present invention relates to a remote drug injecting device for administrating drugs to an animal.

BACKGROUND OF THE INVENTION

The advent of the wildlife rabies epidemic in the East has severely taxed law enforcement and animal control departments from Florida to New Hampshire. The problem has recently become such a concern that an "800" phone number has been established in at least one state to provide information to the public by answering questions on rabies related problems.

If a person is bitten by an animal and the animal is rabid, a post exposure vaccine must be given to avoid the fatal disease in humans. Since the treatment is expensive, painful and possibly life threatening to someone with other preexisting medical conditions, it is imperative that the animal suspected of carrying the virus be tested for the rabies virus. The brain of a potentially infected animal can be tested for the rabies virus if the animal is captured. Presently, the animals are frequently captured by shooting. Shooting, however, may be construed as an inhumane method of euthanizing animals and in many situations may endanger bystanders. Shooting, furthermore, can destroy the brain which is used for testing for infection with the rabies virus. Injection of the animals offers a more humane method of euthanizing the animal and provides a method of euthanizing which can be practiced without endangering bystanders.

There are several devices currently available for remotely injecting animals with solutions to inoculate, medicate or euthanize animals. The injection solutions will hereafter be referred to as drugs irrespective of their functions. These injection devices have been developed primarily for use by the veterinarian community. These injection devices are expensive, complex in design and can be cumbersome to load in the field. These limitations make the devices currently available ill-suited for use by the law enforcement officers or animal control officers who are responsible for capturing potentially rabid animals or for conservation officers who may wish to sedate an animal for observation.

One of the early remote animal injecting devices is described in U.S. Pat. No. 3,494,358 which discloses a design developed for veterinarians. The device uses a standard syringe held in place with multiple clips and has a complex triggering mechanism which must be cocked before the device is ready for service. The complexity of the device makes loading the device difficult. Furthermore, the complexity of the device makes it unreliable in field conditions where the injection device may be stored in hostile environments such as the back of an open truck. Additionally, the loading and removal of the syringe in the injection device is difficult.

More recent patents teach somewhat simpler injection devices. U.S. Pat. No. 3,780,734 has simplified the injection device, however, the syringe must be loaded in a canister before it can be used. Thus, a setup time is required before the device can be used. U.S. Pat. No. 3,840,007 teaches another injection device which suffers from a similar problem as that of the '734 patent since the syringe is loaded into a two-part canister.

U.S. Pat. No. 3,880,162 discloses a remote drug injection device having a syringe barrel which is placed in a metal sheath to provide stability and strength to the barrel. The standard plunger designed for the syringe barrel is replaced by a specially manufactured pole plunger, which is a pole having one end contoured to form a plunger. Since the syringe barrel is maintained in the metal sheath by friction, insertion and removal of the syringe can be difficult. If the metal sheath is too loose, it will not adequately grip the syringe while in use. If the sheath is too tight, it may be difficult to remove the syringe barrel and needle from the sheath. This becomes a particular concern when the animal the device has been used on is suspected of having an infectious disease and prolonged contact with the used syringe with the possibility of a needle puncture could endanger the person injecting the animal.

One of the injection devices which is currently available through Carl Jackson of Colebrook, N.H. is a device which employs many of the elements of the injection device of the '162 patent but eliminates the metal sheath by using the injection barrel and plunger such as taught in U.S. Pat. No. 3,209,695. The '695 patent discloses an injection projectile which can be fired at the animal. Once the needle penetrates the animal, a small explosive charge is detonated which actuates the plunger injecting the drug into the animal. Loading the drug injection device of the '695 patent is difficult since the appropriate dosage must be measured and poured into the barrel. In the injection device currently sold by Carl Jackson, the chamber of the '695 patent replaces the syringe of the '162 patent and the explosive charge of the '695 patent has been replaced by a plunger pole, similar to the pole taught by the '162 patent. The resulting device is difficult to load since the front cap with the needle attached to it has to be unscrewed and the drug poured into the barrel. Unscrewing the endcap can be particularly difficult in field conditions if dirt or corrosion gets into the threads.

Thus, there is a need for a simple injection device for remote drug injection of animals which can be quickly loaded with a syringe having a standard barrel and plunger. The injection device also needs to be sufficiently simple to avoid damage to its mechanism under the conditions of field use.

OBJECTS OF THE INVENTION

An object of the invention is to provide a simple injection device which employs a standard syringe for remotely administering drugs to animals.

Another object of the invention is to provide a remote drug injection device which has few parts and can be readily manufactured.

Yet another object of the invention is to provide a remote drug injection device which is easy to load.

It is still another object of the invention to provide a remote drug injection device where contact with the drug can be avoided.

Still another object of the invention is to provide a remote drug injection device where the drug can be predispensed in a sealed syringe.

A further object of the invention is to provide a remote drug injection device which is easy to unload.

Yet another object of this invention is to provide a remote drug injection device which minimizes the risk to the party using the injection device of needle punctures.

Another object of this invention is to provide a remote drug injection device which can be fabricated from materials not subject to corrosion allowing the injection device to be stored in field conditions for extended periods without risk of malfunction due to rust or corrosion.

Still another object of the invention is to provide a remote drug injection device which is simple and reliable to operate.

These and other objects of the invention will be obvious in view of the following description, drawings and claims.

SUMMARY OF THE INVENTION

The present invention provides a device for remotely administrating a drug to an animal. The device of the present invention employs a standard hypodermic syringe having a barrel with a chamber therein. The barrel attaches to a needle and a plunger slidably engages the chamber of the barrel. The remote drug injection device, in an elementary form, has a tube which terminates in a front rim and a rear rim. The tube has three sections; a syringe section, a plunger section and a rear section. The syringe section of the tube has a longitudinal syringe engaging passage which is configured to grippably engage the syringe.

The plunger section of the tube adjoins the syringe section. The plunger section has a plunger passage therein axially aligned with the longitudinal syringe engaging passage. The plunger passage has a cross section of sufficient size to accommodate the plunger of the syringe. The plunger passage is designed to accommodate the plunger when the plunger is extended and the chamber of the syringe contains the drug for injection.

The rear section adjoins the plunger section and has a rear section passage which is axially aligned with the longitudinal syringe engaging passage and the plunger passage so that a common tube axis exists for the three sections of the tube.

A syringe insertion passage is provided in the tube which traverses the longitudinal syringe engaging passage of the syringe section of the tube. The syringe insertion passage has a central axis which intersects the tube axis.

The tube is provided with multiple openings to allow the syringe to be rotated between the syringe insertion passage and the longitudinal syringe engaging passage. The combination of the multiple openings and the multiple passages permits insertion and removal of the syringe and plunger without necessitating an openable syringe holder.

A bottom syringe passage opening is provided which intersects the front rim of the tube and extends into the syringe insertion passage. Similarly, a top syringe passage opening is provided which is diametrically opposed and offset with respect to the bottom syringe passage opening and extends from the syringe insertion passage to the plunger section where it joins a plunger section opening which is provided in the plunger section. Having the passages so positioned allows the syringe barrel having the needle attached thereto and the plunger extending therefrom to be rotated from the syringe insertion passage to the longitudinal syringe engaging passage where the syringe barrel and plunger are aligned with the tube axis.

The top syringe passage opening and the bottom syringe passage opening have a width W and the barrel of the syringe has a diameter D. When the width W of the top and/or bottom syringe passage openings are slightly less than the diameter D of the barrel of the syringe, the barrel can be rotated between the syringe insertion passage and the longitudinal syringe engaging passage by the elastic deformation of either the tube or the syringe or by a combination thereof. Maintaining the width W of the top and/or bottom syringe passage openings less than the diameter D of the barrel of the syringe will assure that the syringe will be gripped by the syringe section and will not be unintentionally disengaged.

The elastic deformation needed to move the syringe between the central axis of the syringe insertion passage and the tube axis will be, in part, a function of the width W of the syringe passage openings in the syringe section of the tube. When the openings have a width W and the syringe barrel has a diameter D, the diameter D should be larger than W and when a flexible plastic syringe is used and the tube is considerably more rigid than the syringe, it is preferred that W be close to D. Maintaining this ratio assures that the syringe can be readily moved between the syringe insertion passage and the longitudinal syringe engaging passage.

While it is generally preferred to have the width W of the syringe passage openings in the tube less than the diameter D of the barrel of the syringe, there are occasions depending upon the rigidity of the barrel of the syringe where maintaining W less than D will require the application of an excessive force to pass the barrel of the syringe in the syringe passage openings, making it difficult to load and unload the tube with the syringe. If the barrel of the syringe is rigid, such as that of a glass barrel, the width W of the syringe passage openings are maintained at the same diameter D of the barrel of the syringe to facilitate passing the barrel of the syringe through the syringe passage openings.

Another advantage of an embodiment where the width W of the syringe passage openings is the same as the diameter D of the barrel is that it is particularly well suited for fabrication by injection molding. Having the width W of the syringe passage openings the same as the diameter D of the barrel provides syringe passages which avoid re-entrant angles and allow the tube to be injection molded using a simple two part mold.

For injection molded tubes and other tubes where the width W of the openings are the same as the diameter D of the barrel, the tube has a longitudinal syringe engaging passage having a front longitudinal syringe engaging cavity and a rear longitudinal syringe engaging cavity. An inter-cavity region remains between the front longitudinal syringe engaging cavity and the rear longitudinal syringe engaging cavity. A longitudinal cylindrical passage lying on the axis of the tube passes through the inter-cavity region. The longitudinal cylindrical passage in combination with the front longitudinal syringe engaging cavity and the rear longitudinal syringe engaging cavity form the longitudinal syringe engaging passage for containment of the syringe. A cylindrical insertion passage, having an axis which intersects the tube axis, also passes though the inter-cavity region and intersects the front longitudinal syringe engaging cavity and the rear longitudinal syringe engaging cavity. The cylindrical insertion passage provides the syringe insertion passage. Because of the curvature of the two intersecting cylindrical passages, two pairs of protrusions will result at the intersection of the two cylindrical passages. These pyramidal-shaped protrusions serve to maintain the syringe in the longitudinal syringe engaging passage or the syringe insertion passage. In this embodiment, in which the side walls have no re-entrant angles, there is no gripping action provided by the front longitudinal syringe engaging cavity. Since the walls of the cavities will not provide gripping support to the syringe, the protrusions serve to contain the syringe in the longitudinal syringe engaging passage. These protrusions serve to maintain the syringe in the longitudinal syringe engaging passage and the syringe insertion passage. Furthermore, when rotating the syringe from the syringe insertion passage to the longitudinal syringe engaging passage the protrusions will allow the syringe to snap from one passage to the other.

It is preferred that a finger port be provided to better distribute the force needed to rotate the syringe between the tube axis and the central axis of the syringe insertion passage. The finger port, if positioned diametrically opposed to the bottom syringe passage opening and directly above the same allows pressure to be applied to the syringe barrel to assist in moving the syringe from the longitudinal syringe engaging passage to the syringe insertion passage. This distribution of the force becomes more important as the size difference between the width W and barrel diameter D increases or where the protrusions between the intersecting cylindrical passages forming part of the longitudinal syringe engaging passage and the syringe insertion passage are large.

A shaft is provided which slidably engages the rear section passage of the tube and is axially aligned with the plunger when the syringe is engaged by the longitudinal syringe engaging passage. Preferably, means for retaining the shaft in the rear section passage are provided. Such means can be provided by an O-ring seated in a circumferential groove in the shaft or resiliently mounted barbs which protrude from the shaft.

As the distance from the animal increases, it is preferable that the syringe section of the tube be tapered such that the front rim provides an area of minimum cross section. This taper allows the needle to pierce the animal at a more oblique angle since interference from the tube will be reduced.

To further stabilize the needle to avoid a bending moment in the junction between the needle and the barrel when the needle is being inserted into the animal, a partition is preferably provided which is mounted in the longitudinal syringe engaging passage. The partition is positioned such that it will be in close proximity to the needle/barrel junction when the hypodermic syringe is engaged in the longitudinal syringe engaging passage. A slot is provided in the partition which extends downward from the tube axis to the bottom syringe passage opening.

Standard hypodermic syringes designed for hand use usually have a flange for gripping the barrel with the user's fingers when depressing the plunger with the thumb. When a flange is included as part of the syringe, a flange engaging slot is provided to accommodate the flange. The flange engaging slot which engages the flange further stabilizes the syringe when the plunger is being advanced by the shaft.

For injection devices where the shaft is long, for example greater than about three feet, it is further preferred that the tube handle be provided to the tube for positioning the needle with respect to the animal to be injected. When a tube handle is employed, the shaft is no longer used to position the tube, and the function of the shaft is limited to providing the motivating force for advancing the plunger. When the tube handle is employed, the handle is preferably coaxial with the tube axis and it is secured to the tube at one end. The shaft resides in the tube handle and extends beyond it for a distance sufficient to assure that the plunger can be fully depressed to eject the drug contained in the barrel of the syringe.

BRIEF DESCRIPTION OF THE FIGURES

FIG. 1 shows a plunger of the syringe in a loaded position where the plunger fully occupies the plunger section. FIG. 2 shows the syringe after it has been purged of the drug, in which case the shaft has been moved forward. FIG. 3 shows the syringe after the drug has been purged and the shaft has been moved away from the plunger so that the syringe can be removed from the tube.

FIG. 4 is a view of the section 4—4 of FIG. 1 shown with the syringe positioned in a longitudinal syringe engaging passage.

FIG. 5 is the view of FIG. 4 where the syringe is shown in a syringe insertion passage prior to being rotated into the longitudinal syringe engaging passage.

FIG. 6 is an enlargement of the circled area of FIG. 5 which shows an O-ring used to maintain the shaft in the rear section passage and a circumferential O-ring groove on the shaft.

FIG. 7 shows a bottom opening provided in the tube which cooperates with a top opening shown in FIG. 8 to permit transfer of a syringe between the syringe insertion passage and the longitudinal syringe engaging passage.

FIG. 13 shows the plug in the safety position. The protective plug is maintained in the position as shown prior to readying the injection device for injecting an animal.

BEST MODE FOR CARRYING THE INVENTION INTO PRACTICE

Figure 1:
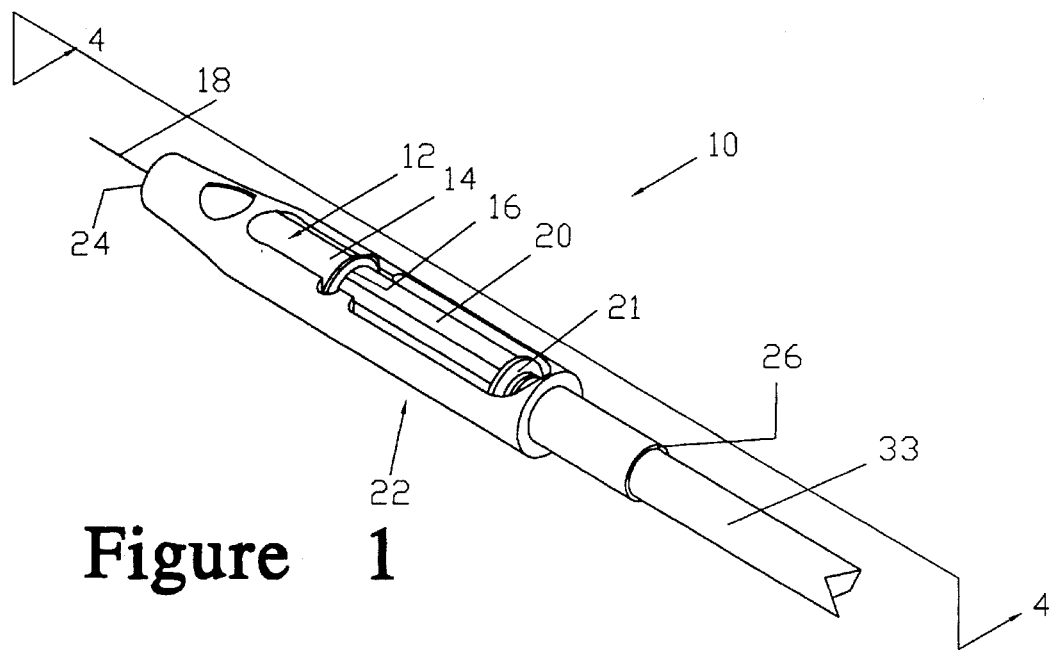
FIGS. 1, 2 and 3 are isometric views of one embodiment of a remote drug injecting device of the present invention. This embodiment employs a standard hypodermic syringe with a syringe barrel and a plunger. The device has a tube having a syringe section, a plunger section and a rear section. The syringe is shown in a longitudinal syringe engaging passage of the tube. A shaft is slidably engaged with a rear section passage of the tube.
Figure 2:
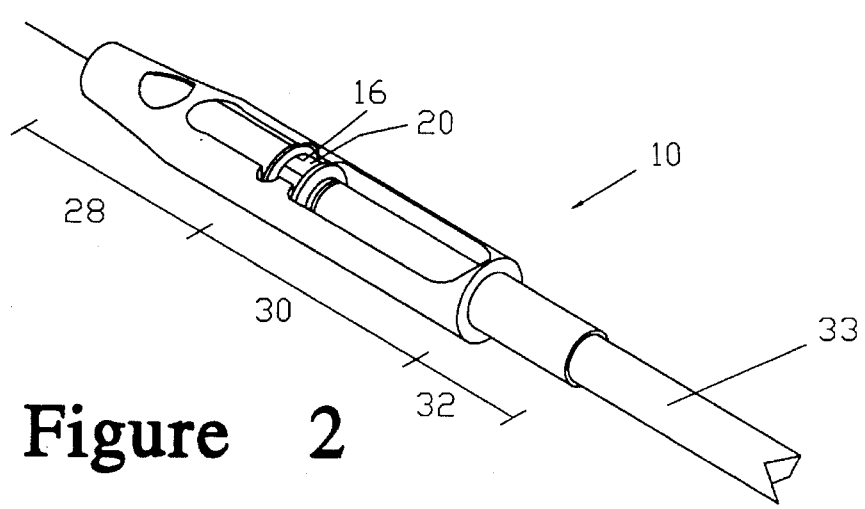
Figure 3:
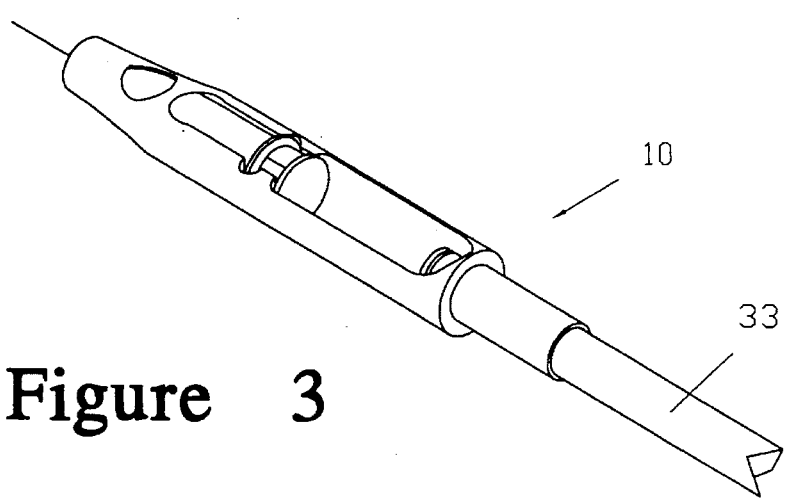

FIGS. 1 through 3 represent one embodiment of a remote drug injection device 10 of the present invention. The remote drug injection device 10 employs a standard hypodermic syringe 12. The syringe 12 has a barrel 14 having a chamber 16. The barrel 14 attaches to a needle 18 which communicates with the chamber 16 of the barrel 14 of the syringe 12. A plunger 20 is provided which has a thumb pad 21. The plunger 20 slidably engages the chamber 16 of the barrel 14. The remote drug injection device 10 has a tube 22 which has a front rim 24 and a rear rim 26. The tube 22 has three sections labeled in FIG. 2. The sections are: a syringe section 28, a plunger section 30 and a rear section 32. FIGS. 1 through 3 illustrate different stages of readiness of the remote drug injection device 10. FIG. 1 illustrates the syringe 12 in the tube 22 with the syringe 12 loaded with a drug to be injected. The plunger 20 extends into the plunger section 30 and is engaged by a shaft 33. FIG. 2 illustrates the remote drug injection device 10 after an animal has been injected and the syringe 12 is spent. In this state of readiness, the shaft 33 has extended into the plunger section 30 and advanced the plunger 20 into the chamber 16. FIG. 3 illustrates the remote drug injection device 10 after injection of an animal where the shaft 33 has been withdrawn from the plunger section 30 to provide access to remove the spent syringe 12.

FIG. 4 shows a cross section 4—4 of FIG. 1 illustrating additional details of this embodiment of the invention. The syringe section 28 of the tube 22 has a longitudinal syringe engaging passage 34 configured to grippably engage the barrel 14 of the standard hypodermic syringe 12. The plunger section 30, which adjoins the syringe section 28, has a plunger passage 35 with a cross section sufficient to accommodate the plunger 20 and the thumb pad 21.

The tube 22 terminates in the rear section 32 having a rear section passage 36 contained therein. The longitudinal syringe engaging passage 34, the plunger passage 35 and the rear section passage 36 have a common axis forming a tube axis 40. For standard syringes designed for hand use, such as illustrated in FIGS. 1 through 5, a flange 42 is provided for gripping with the fingers, stabilizing the syringe 12 as the plunger 20 is depressed by the thumb which engages the thumb pad 21. A flange engaging slot 44 is provided in the tube 22 to accommodate the flange 42. The flange engaging slot 44, in combination with the gripping action of the longitudinal syringe engaging passage 34, maintains the syringe 12 fixed in the tube 22 as the shaft 33 is advanced causing the drug to be injected into the animal.

The syringe section 28 of the tube 22, in addition to having the longitudinal syringe engaging passage 34, has a syringe insertion passage 46 which traverses the tube 22 and intersects the longitudinal syringe engaging passage 34. The syringe insertion passage 46 has a central axis 48 which intersects the tube axis 40.

FIG. 5 shows the syringe 12 positioned in the syringe insertion passage 46. To permit rotation of the syringe 12 between the syringe insertion passage 46 and the longitudinal syringe engaging passage 34, multiple openings are provided in the tube 22. These openings allow the barrel 14 to be swung into the longitudinal syringe engaging passage 34 and simultaneously allow the plunger 20 to be swung into the plunger passage 35. This repositioning of the syringe 12 can be accomplished without opening the tube 22, thus facilitating convenient field loading of the remote drug injection device 10.

Figure 7:
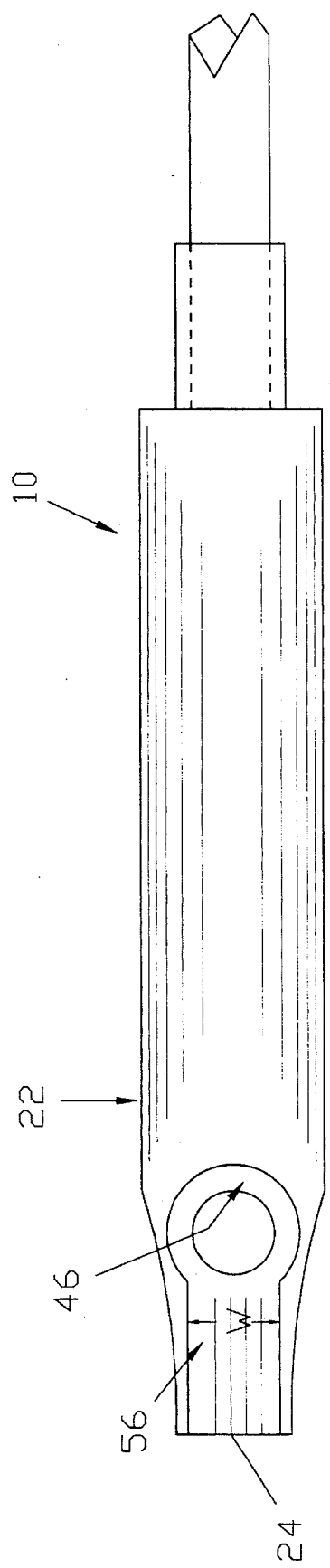
FIG. 7 is a bottom view of the injection device of FIGS. 1 through 3 without a syringe positioned in the device.
Figure 8:
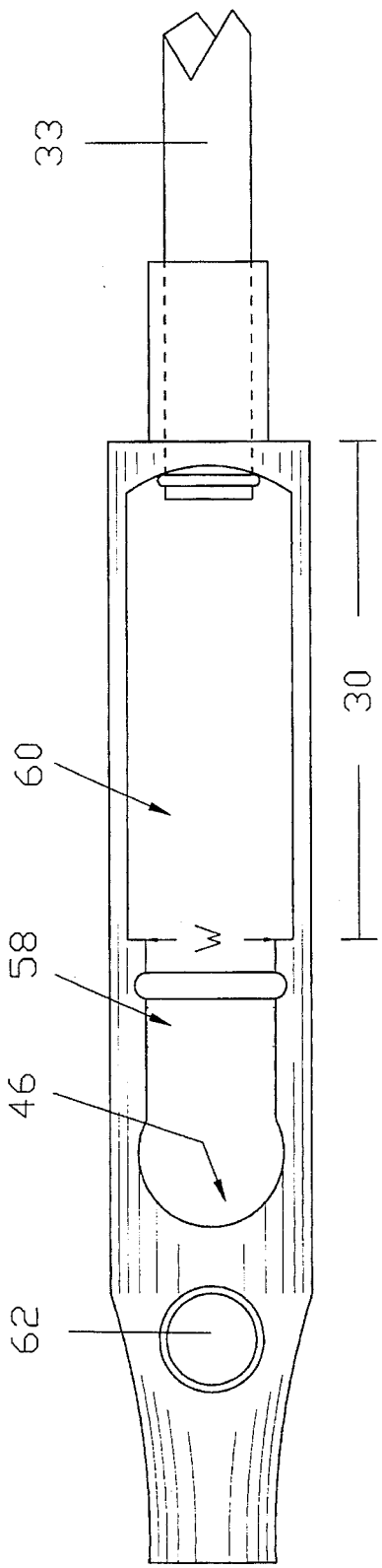
FIG. 8 is a top view of the injection device of FIGS. 1 through 3, without the syringe positioned in the device. A finger port is provided which allows a force to be applied to the syringe to assist in transferring the syringe from the longitudinal syringe engaging passage to the syringe insertion passage.

A bottom syringe passage opening 56 (numbered in FIGS. 4, 5 and 7) is provided which extends from the front rim 24 of the tube 22 to the syringe insertion passage 46. The bottom syringe passage opening 56 allows the needle 18 and front portion of the syringe 12 to be rotated between the syringe insertion passage 46 and the longitudinal syringe engaging passage 34. Similarly, a top syringe passage opening 58 (numbered in FIGS. 4 and 8), is provided which is diametrically opposed and offset with respect to the bottom syringe passage opening 56. The top syringe passage opening 58 extends from the syringe insertion passage 46 into the plunger section 30 where the top syringe passage opening 58 joins a plunger section opening 60 (best shown in FIG. 8). The top syringe passage opening 58 allows the rear portion of the barrel 14 to be rotated between the syringe insertion passage 46 and the longitudinal syringe engaging passage 34. The plunger section opening 60 allows the extended plunger 20 and the thumb pad 21 to swing into the plunger passage 35 when the barrel 14 of the syringe 12 swings into the longitudinal syringe engaging passage 34. As can be seen, having the openings 56, 58, and 60 so located allows the syringe barrel 14 and the plunger 20 with the thumb pad 21 to be rotated from the syringe insertion passage 46 to the longitudinal syringe engaging passage 34 and the plunger passage 34 and the plunger passage 35 without requiring the tube 22 to be openable.

The bottom syringe passage opening 56 and the top syringe passage opening 58 preferably both have a width W (shown in FIGS. 7 and 8) which is slightly less than the diameter D of the syringe barrel 14 (shown in FIG. 5). Although the width W of these passage openings (56 and 58) is slightly less than the diameter D of the barrel 14, the barrel 14 can be rotated between the syringe insertion passage 46 and the longitudinal syringe engaging passage 34 by elastic deformation of either the tube 22, the syringe barrel 14 or a combination thereof. As the difference between W and D increases or, alternatively, the elastic modulus of the tube 22 and the barrel 14 are both high, a finger port 62 allows additional force to be applied to the syringe 12 to aid in the transfer of the syringe 12 from the longitudinal syringe engaging passage 34 to the syringe insertion passage 46. The finger port 62 allows access to the barrel 14 so that the finger pressure on the barrel 14 can be used to assist in raising the barrel 14 from the longitudinal syringe engaging passage 34 to the syringe insertion passage 46, an action required prior to disengaging a spent syringe 12 from the tube 22.

Referring again to FIG. 5, it is further preferred that the central axis 48 of the syringe insertion passage 46 be maintained at an angle B between about 30° and 40° with respect to the tube axis 40. Maintaining β within this range assures a sufficient offset is maintained between the sidewalls of the syringe insertion passage 46 and the longitudinal syringe engaging passage 34 to limit the discontinuity which results in the surface which is generated by the intersection of the longitudinal syringe engaging passage 34 and the syringe insertion passage 46. Limiting the size of this discontinuity assures the barrel 14 of the syringe 12 can be snapped into and out of the longitudinal syringe engaging passage 34 without undue force. Maintaining the angle B in the range of 30° to 40° also assists in the visual alignment of the flange 42 with respect to the flange engaging slot 44 so that they can be prealigned such that as the barrel 14 is snapped into the longitudinal syringe engaging passage 34 the flange 42 will slide into the flange engaging slot 44.

The angular range for which the needle 18 will penetrate an animal successfully will increase if the cross section of the front rim 24 of the tube 22 is minimized. In embodiments used in all the figures, the sidewall of the tube 22 is tapered so that its thickness decreases as the sidewall of the tube 22 approaches the front rim 24 resulting in a reduced cross section of the front rim 24 of the tube 22. In this preferred configuration, for a given extension of the needle 18 beyond the front rim 24 of the tube 22, the range of angular penetration of the needle 18 will increase.

Figure 9:
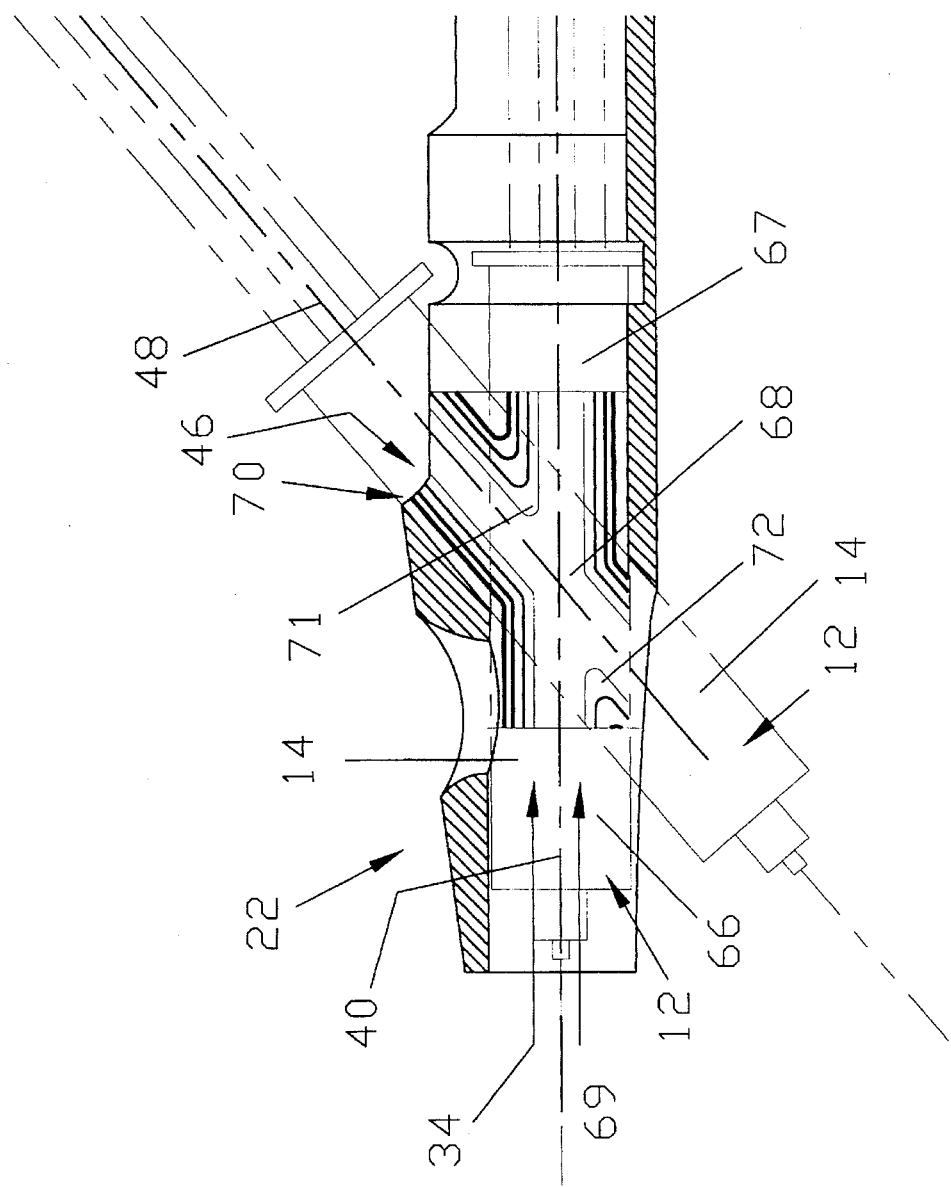
FIG. 9 is a similar view to FIGS. 4 and 5 and illustrates an embodiment of the present invention. In this embodiment, the longitudinal syringe engaging passage has three sections, a front longitudinal syringe engaging cavity and a rear longitudinal syringe engaging cavity which are connected by a longitudinal cylindrical passage which passes through an inter-cavity region.

FIG. 9 illustrates another embodiment of the present invention which employs the tube 22 which is well suited for fabrication by injection molding. The longitudinal syringe engaging passage 34 is composed of a front longitudinal syringe engaging cavity 66 and a rear longitudinal syringe engaging cavity 67. An inter-cavity region 68 is positioned between the front longitudinal syringe engaging cavity 66 and the rear longitudinal syringe engaging cavity 67. A longitudinal cylindrical passage 69 passes through the inter-cavity region 68 and lies on the tube axis 40 of the tube 22. The longitudinal cylindrical passage 69 in combination with the front longitudinal syringe engaging cavity 66 and the rear longitudinal syringe engaging cavity 67, forms the longitudinal syringe engaging passage 34 for containment of the syringe 12. A cylindrical insertion passage 70 also passes through the inter-cavity region 68, intersecting the front longitudinal syringe engaging cavity 66 and the rear longitudinal syringe engaging cavity 67. The cylindrical insertion passage 70 has the central axis 48 which intersects the tube axis 40 and serves as the syringe insertion passage 46. Because of the curvature of the two intersecting cylindrical passages (69 and 70), their intersection generates two pairs of protrusions which extend into the intersection of the two cylindrical passages (69 and 70). An upper pair of protrusions 71 form pyramidal shaped areas which are terminated by the rear longitudinal syringe engaging cavity 67. Similarly, a lower pair of protrusions 72 form pyramidal shaped areas which are terminated by the front longitudinal syringe engaging cavity 66.

When the cavities 66 and 67 are free of re-entrant angles, the design is well suited for injection molding of the tube 22. Since no re-entrant angles exist, there is no gripping action provided by the walls of the front longitudinal syringe engaging cavity 66 or the rear longitudinal syringe engaging cavity 67. Since the walls of the cavities (66 and 67) will not provide gripping support to the syringe 12, the protrusions (71 and 72) serve to contain the syringe in the longitudinal syringe engaging passage 34. These protrusions (71 and 72) serve to lock the syringe 12 in the longitudinal syringe engaging passage 34 and the syringe insertion passage 46. Furthermore, when rotating the barrel 14 from the longitudinal syringe engaging passage 34 to the syringe insertion passage 46, the protrusions (71 and 72) will allow the syringe 12 to snap from one passage to the other.

Turning attention again to FIGS. 4 and 5, the shaft 33 which slidably engages the rear section passage 36 employs an O-ring 74, as a means for maintaining the shaft 33 in the plunger passage 35. The O-ring 74 engages a circumferential O-ring groove 75, shown in FIG. 6, and is maintained on the shaft 33 by the groove 75. The O-ring 74, in turn, serves as a stop to maintain the shaft 33 in the rear section passage 36 of the tube 22.

Figure 10:
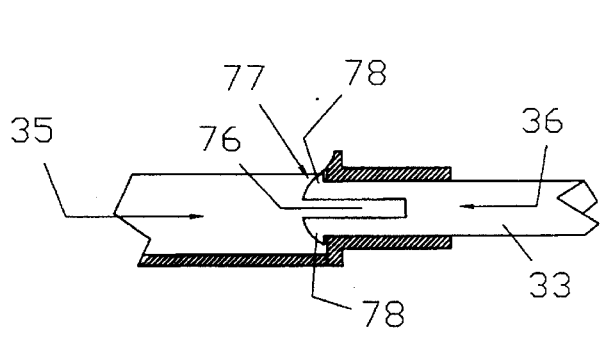
FIG. 10 is a partial side view in cross-section of a tube of another embodiment of the present invention which has a shaft which employs barbs as a means for retaining the shaft in the rear section passage of the tube.

FIG. 10 illustrates an alternative means for retaining the shaft 33 in the rear section passage 36. In this embodiment, the shaft 33 is provided with a shaft slot 76 which extends to a plunger engaging end 77 of the shaft 33. The plunger engaging end 77 resides in and is maintained in the plunger passage 35 by shaft barbs 78 which extend beyond the periphery of the shaft 33 when the shaft slot 76 is open. When the plunger engaging end 77 is compressed such that the shaft slot 76 closes, the shaft barbs 78 can pass through the rear section passage 36 allowing the shaft 33 to be removed from the tube 22.

Figure 11:
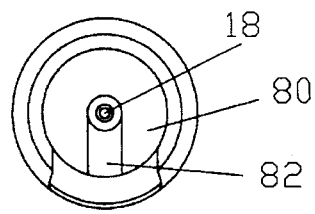
FIG. 11 shows a front view of another embodiment of the remote drug injecting device of the present invention. In this embodiment, a partition is provided in the longitudinal syringe engaging passage. The partition is positioned to engage the needle at a hub which serves as the needle/barrel junction thereby reducing the bending moments on the needle which can result from the animal moving as it is being injected.
Figure 12:
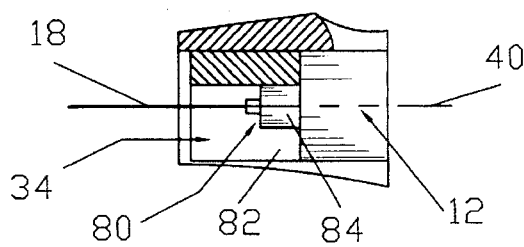
FIG. 12 is a side sectional view of FIG. 11 which shows the partition engaged with the hub of the needle minimizing the moment on the needle/barrel junction.

FIGS. 11 and 12 illustrate another embodiment of the invention where the needle 18 of the syringe 12 is stabilized with respect to the barrel 14 to reduce the likelihood of a fracture therebetween caused by bending moments resulting from the animal moving after the needle 18 has been inserted. A partition 80 is provided, which attaches to the longitudinal syringe engaging passage 34 and is substantially normal to the tube axis 40. The partition 80 has a slot 82 into which the needle 18 slides as the barrel 14 is rotated from the syringe insertion passage 46 (best shown in FIG. 5) to the longitudinal syringe engaging passage 34. The needle 18 has a needle hub 84. The slot 82 is configured to engage the needle hub 84 when the syringe 12 is maintained in the longitudinal syringe engaging passage 34. Having the slot 82 so positioned and configured assures that maximum support will be given to the needle hub 84 which forms the needle/barrel junction.

Figure 13:
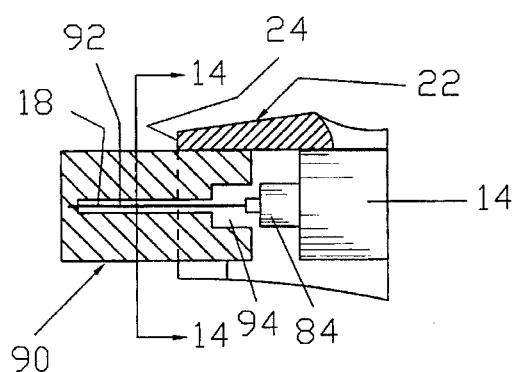
FIG. 13 is a section of a side view of a front portion of a tube which forms part of another embodiment of the injection device of the present invention. This embodiment employs a longitudinal syringe engaging passage plug to stabilize the needle from bending moments as well as to provide a protective cover for the needle. The plug engages the front rim of the tube and serves three functions: it protects the needle from the elements, dirt, dust and the like; it avoids accidental puncture of the user by the device; and it serves to stabilize the needle against bending moments resulting from the movement of the animal while it is being injected.
Figure 14:
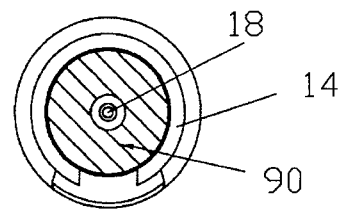
FIG. 14 is a section 14—14 of FIG. 13 illustrating the relative positions of the needle, the longitudinal syringe engaging passage plug and its relationship to the longitudinal syringe engaging passage.
Figure 15:
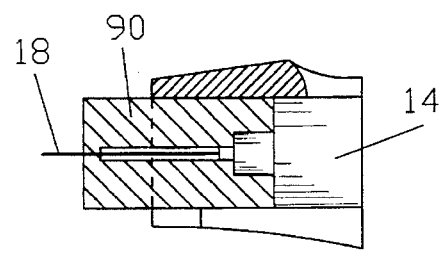
FIG. 15 is a similar view to the view of FIG. 13 except the protective plug has been moved to a ready position where the protective plug contacts the syringe and the needle is exposed. A supporting pocket surrounds the hub of the needle which serves as the needle/barrel junction reducing the moment at the needle/barrel junction resulting from movement of the animal as it is being injected.

FIGS. 13 through 15 provide another embodiment offering an alternative means to stabilize the needle/barrel junction. In this embodiment, a plug 90 is provided which engages the front rim 24 of the tube 22.

The plug 90 has a blind passage 92 therein into which the needle 18 will fit when the plug 90 is partially engaged in the longitudinal syringe engaging passage 34. Having the plug 90 partially engaged as illustrated in FIG. 13 provides a cover for the needle 18 and protects the user from accidental puncture by the needle 18. The plug 90 has a pocket 94 configured to engage the needle hub 84 when the plug 90 is fully engaged and brought into contact with the barrel 14. Referring to FIG. 15, the needle 18 will extend beyond the plug 90 when the plug 90 is in contact with the barrel 14.

Figure 16:
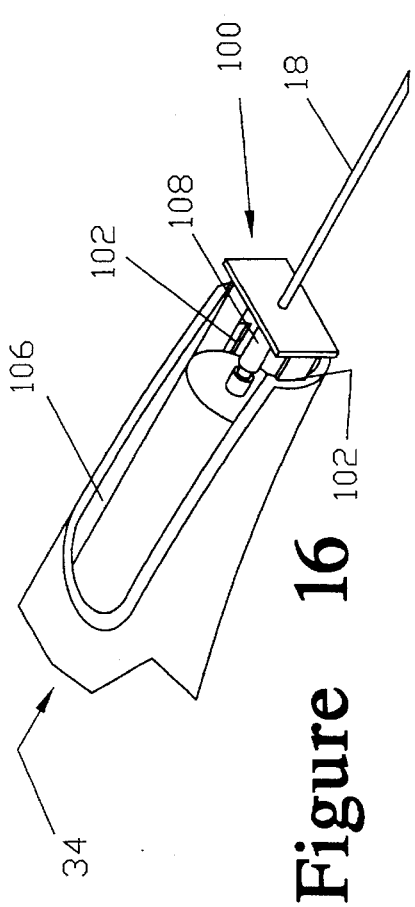
FIG. 16 is an isometric view of an embodiment which employs, a protective clip to further stabilize the needle of the syringe. The view shows the front of the tube with the bottom facing up. The clip is adjustable and provides two functions. It protects the needle from bending moments and serves to protect the user from accidental puncture by the needle. In this view, the clip is in a retracted position, closest to the front rim of the tube.

FIGS. 16 through 19 illustrate another embodiment of a means for stabilizing the needle/barrel junction which will also provide protection from accidental puncture of the user by the needle 18. In this embodiment, a clip 100 replaces the plug 90. The clip 100 can be brought into close proximity to the front rim 24 of the tube 22 and will substantially increase the angle of entry of the needle 18 into the animal. The clip 100 is configured with clip arms 101 which slidably engage channels 102 in a sidewall 106 of the longitudinal syringe engaging passage 34. The clip 100 provides support to the needle 18 and, when positioned as shown in FIG. 16, exposes substantially more of the needle 18 than the plug 90 does, thus providing a greater range in the angle of penetration. Substantial support for the needle 18 is provided by a needle guide tube 108 which supports the needle 18 between the clip 100 and the syringe 12.

Figure 17:
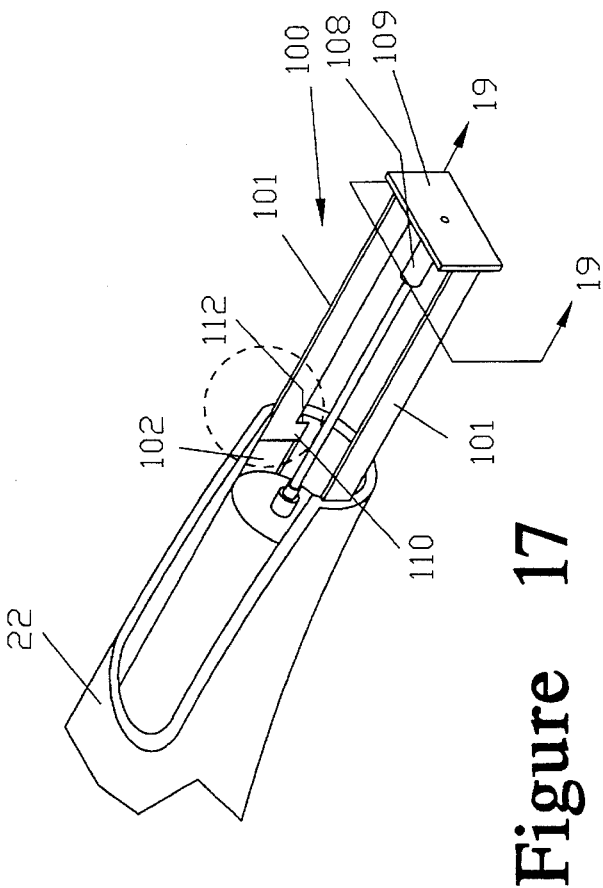
FIG. 17 is similar to the view of FIG. 16; however, in this view, the protective clip is shown at maximum extension. The clip also has clip lugs which prevent the clip from becoming disengaged from the tube.

As shown in FIG. 17, the clip arms 101 attach to a clip front plate 109. The clip arms 101 engage the channels 102 and terminate in clip lugs 110 which engage a channel notches 112. The clip lugs 110 prevent the clip 100 from being disengaged from the tube 22. Insertion or removal of the clip 100 is accomplished by squeezing the clip arms 101 together and engaging or disengaging the clip lugs 110 from the channel notches 112.

Figure 18:
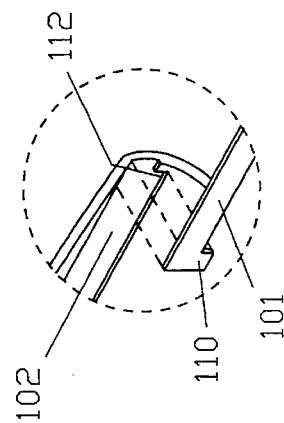
FIG. 18 is an enlargement of the region circled in FIG. 17 which best shows the clip lugs engaging a channel notch on the sidewall of the tube.

FIG. 18 is an enlargement of the region circled in FIG. 17 which best shows the clip lugs 110 engaging the channel notch 112 on the sidewall 106 of the tube 22. It should be appreciated that while the clip lugs 110 are shown protruding below the clip arms 101, they could also be positioned above or laterally from the clip arms 101.

Figure 19:
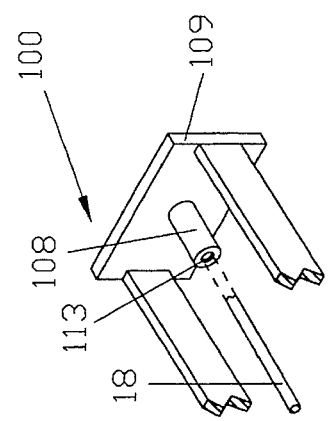
FIG. 19 is an isometric rear view of the section 19—19 of FIG. 17, which shows a needle point guide which attaches to the clip and assures registry of the needle with a needle passage through the clip.

In a this embodiment, the guide tube 108 is mounted on the clip front plate 109 of the clip 100 as shown in FIG. 19. Preferably, the guide tube 108 has its free end 113 flared to facilitate insertion of the needle 18 into the guide tube 108.

Figure 20:
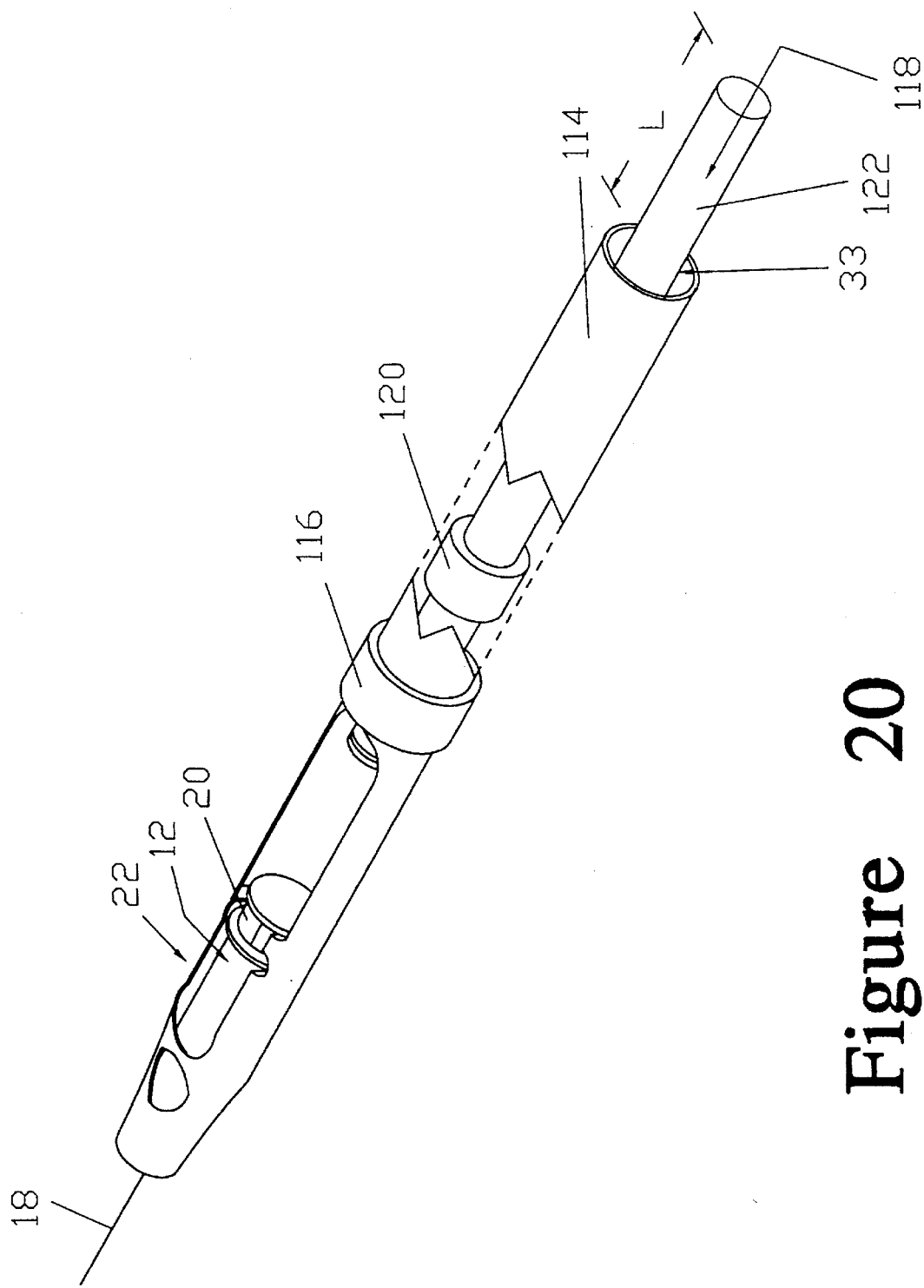
FIG. 20 is another embodiment of the invention which employs a tube similar to the embodiment illustrated in FIGS. 1 through 3. This embodiment differs in part from the embodiment illustrated in FIGS. 1 through 3 in that a hollow handle is provided which attaches to the tube. The hollow handle is employed to position the tube with respect to the animal. A shaft, which is axially aligned with the hollow tubular handle, is provided to depress the plunger and inject the animal.

FIG. 20 illustrates another embodiment of the present invention which is particularly well suited for situations where a substantial distance between the user and the animal (e.g. three feet or more) is required. When a substantial distance from the animal being injected is maintained, it is preferred not to use the shaft 33 to position the tube 22. At extended distances, it is possible to strike a glancing blow when trying to inject the animal which could advance the plunger 20 without having the needle 18 properly embedded in the animal. When the distance from the animal will be substantial, it is preferred to provide a separate handle which is affixed to the tube 22. This allows the function of positioning the tube 22 and inserting of the needle 18 to be separately controlled from the function of injecting the animal with the drug. The embodiment of FIG. 20 employs a hollow tube handle 114 which is coupled to the tube 22 by a handle coupling 116. A coupling such as a threaded or bayonet coupling can be used.

The handle 114 allows the needle 18 to be inserted into the animal prior to the injection of the animal with the drug while the shaft 33 is carried in a central passage 118 in the handle 114. The shaft 33, which extends beyond the handle 114, is advanced to administer the drug. Once the needle 18 has punctured the animal, the shaft 33 should have a length L sufficient to allow the shaft 33 to be advanced a sufficient distance to fully administer the drug contained in the syringe 12.

A shaft engaging coupling 120 which employs fastening means such as threads or bayonet locks is provided to attach a shaft extender 120 to provide shafts 33 of varying length to the tube 22. The selection of the shaft extender 122 is made so as to assure the shaft 33 will extend beyond the handle 114.

While the present invention has been described in terms of preferred embodiments, it should be understood that substitutions and changes may be made by one skilled in the art without departing from the spirit of the invention.

What I claim is:

1. A remote drug injecting device for remotely administering a drug to an animal which can employ a standard hypodermic syringe having a barrel and a plunger which slidably engages the barrel, comprising:

a tube having a front rim, a rear rim and a tube axis, said tube having,
   a syringe section having a longitudinal cylindrical syringe engaging passage configured to grippably engage the syringe,
   a plunger section having a plunger passage having a cross section configured to accommodate the plunger, and
   a rear section having a rear passage,
      said longitudinal cylindrical syringe engaging passage, said plunger passage, and said rear passage lying on said tube axis;

a cylindrical syringe insertion passage passing through said syringe section of said tube, said cylindrical syringe insertion passage having a central axis which intersects said tube axis providing an intersection between said longitudinal cylindrical syringe engaging passing and said cylindrical syringe insertion passage, said cylindrical syringe insertion passage being contoured to be slidably engaged by the syringe and said intersection providing two paired protrusions which extend into said intersection;

a bottom syringe passage opening extending from said front rim of said tube and joining said cylindrical syringe insertion passage;

a top syringe passage opening extending from said cylindrical syringe insertion passage into said plunger section;

a plunger section opening continuing said top syringe passage opening into said plunger section; and a shaft slidably engaging said rear passage of said tube.

2. The remote drug injection device of claim 1 further comprising:

means for maintaining said shaft in said rear section passage.

3. The remote drug injection device of claim 2 wherein said syringe section is tapered such that said front rim provides a section of minimum cross section.

4. The remote drug injection device of claim 3 further comprising:

a finger port in said syringe section of said tube, said finger port being diametrically opposed to said tube bottom opening.

5. The remote drug injection device of claim 4 further comprising:

a handle attached to said tube and extending away from said front rim.

6. The remote drug injecting device of claim 5 wherein said handle is cylindrical and is coaxial with said tube.

7. The remote drug injecting device of claim 2 wherein said means for maintaining said shaft in said rear passage further comprises:

an O-ring which attaches to said shaft.

8. The remote drug injecting device of claim 2 wherein said means for maintaining said shaft in said rear passage further comprises:

resiliently mounted barbs which protrude beyond said shaft.

9. A remote drug injecting device for remotely administering a drug to an animal which can employ a standard hypodermic syringe having a barrel and a plunger which slidably engages the barrel, a needle attached to the syringe providing a needle/barrel junction, the remote drug injecting device comprising:

a tube having a front rim, a rear rim and a tube axis, said tube having,
   a syringe section tapered such that said front rim provides a section of minimum cross section, said syringe section having a longitudinal cylindrical syringe engaging passage configured to grippably engage the syringe,
   a plunger section having a plunger passage having a cross section configured to accommodate the plunger, and
   a rear section having a rear passage,
       said longitudinal cylindrical syringe engaging passage and said plunger passage, and said rear passage lying on said tube axis;

a cylindrical syringe insertion passage passing through said syringe section of said tube, said cylindrical syringe insertion passage having a central axis which intersects said tube axis providing an intersection between said longitudinal cylindrical syringe engaging passage and said cylindrical syringe insertion passage, said cylindrical syringe insertion passage being contoured to be slidably engaged by the syringe and said intersection providing two pairs protrusion which extend into said intersection;

a bottom syringe passage opening extending from said front rim of said tube and joining said cylindrical syringe insertion passage;

a top syringe passage opening extending from said cylindrical syringe insertion passage into said plunger section;

a plunger section opening continuing said top syringe passage opening into said plunger section;

a shaft slidably engaging said rear passage of said tube;

means for maintaining said shaft in said rear section; and means to stabilize the needle/barrel junction.

10. The remote drug injection device of claim 9 where said means to stabilize the needle/barrel junction further comprises:

a partition attaching to said longitudinal syringe engaging passage and substantially normal to said tube axis; and a slot in said partition into which the needle can be rotated,
   said partition and said slot being so positioned such that the needle/barrel junction lies in said slot when the syringe lies in said longitudinal syringe engaging passage.

11. The remote drug injection device of claim 9 wherein said means to stabilize the needle/barrel junction further comprises:

a clip which slidably engages said tube, said clip having a passage therethrough of the needle.

12. A remote drug injection device for remotely administering a drug to an animal which can employ a standard hypodermic syringe having a flange, a barrel and a plunger which slidably engages the barrel, comprising:

a tube having a front rim, a rear rim and a tube axis, said tube having,
   a syringe section tapered such that said front rim provides a section of minimum cross section, said syringe section having a longitudinal cylindrical syringe engaging passage configured to grippably engage the syringe,
   a plunger section having a plunger passage having a cross section configured to accommodate the plunger, and
   a rear section having a rear passage,
       said longitudinal cylindrical syringe engaging passage and said plunger passage, and said rear passage lying on said tube axis, and
   said tube is provided with a flange engaging slot;

a cylindrical syringe insertion passage passing through said syringe section of said tube, said cylindrical syringe insertion passage having a central axis which intersects said tube axis providing an intersection between said longitudinal cylindrical syringe engaging passage and said cylindrical syringe insertion passage, said cylindrical syringe insertion passage being contoured to be slidably engaged by the syringe and said intersection providing two pairs protrusion which extend into said intersection;

a bottom syringe passage opening extending from said front rim of said tube and joining said syringe insertion passage;

a top syringe passage opening extending from said cylindrical syringe insertion passage into said plunger section;

a plunger section opening continuing said top syringe passage opening into said plunger section;

a shaft slidably engaging said rear passage of said tube; and means for maintaining said shaft in said rear section.

13. The remote drug injection device of claim 12 further comprising:

a handle attached to said tube and extending away from said front rim.

14. The remote drug injection device of claim 12 further comprising:

a handle attached to said tube and extending away from said front rim; and a handle coupling employed to connect said tube to said handle.

15. The device of claim 14 wherein:

said shaft has a shaft extender; and a shaft engaging coupling is provided to attach said shaft extender to said shaft.

* * * * *